US012337123B2

(12) United States Patent
Gupta et al.

(10) Patent No.: US 12,337,123 B2
(45) Date of Patent: Jun. 24, 2025

(54) SAFETY INTRAVENOUS CANNULA

(71) Applicant: MedSource Labs, LLC, Chanhassen, MN (US)

(72) Inventors: Neeraj Gupta, Gurgaon (IN); Calvin Todd Fagley, Excelsior, MN (US); Rachel Ann Sender, Eden Prairie, MN (US)

(73) Assignee: MedSource Labs, LLC, Chanhassen, MN (US)

( * ) Notice: Subject to any disclaimer, the term of this patent is extended or adjusted under 35 U.S.C. 154(b) by 214 days.

(21) Appl. No.: 17/551,255

(22) Filed: Dec. 15, 2021

(65) Prior Publication Data
US 2022/0355072 A1 Nov. 10, 2022

(30) Foreign Application Priority Data
May 6, 2021 (IN) .............................. 202111020693

(51) Int. Cl.
*A61M 25/00* (2006.01)
*A61M 25/06* (2006.01)

(52) U.S. Cl.
CPC .... *A61M 25/0097* (2013.01); *A61M 25/0043* (2013.01); *A61M 25/0625* (2013.01); *A61M 25/0662* (2013.01); *A61M 2205/02* (2013.01)

(58) Field of Classification Search
CPC .......... A61M 25/0097; A61M 25/0625; A61M 25/0662; A61M 2205/02; A61M 25/0043; A61M 25/0606; A61M 25/0631
See application file for complete search history.

(56) References Cited

U.S. PATENT DOCUMENTS

| 4,022,191 A | 5/1977 | Jamshidi |
| 4,269,186 A | 5/1981 | Loveless et al. |
| 4,747,831 A | 5/1988 | Kulli |
| 4,762,516 A | 8/1988 | Luther et al. |

(Continued)

FOREIGN PATENT DOCUMENTS

| AU | 2002340363 B2 | 8/2008 |
| CA | 2178267 A1 | 12/1996 |

(Continued)

OTHER PUBLICATIONS

Murty, Y. V. "Use of stainless steels in medical applications." (2003), (p. 288) (Year: 2003).*

(Continued)

*Primary Examiner* — Theodore J Stigell
(74) *Attorney, Agent, or Firm* — Dorsey & Whitney LLP

(57) ABSTRACT

The present invention relates to a cannula comprising a catheter assembly, a body member, an elongated tubular member, a needle hub, and a safety device fixedly connected to a distal end of the elongated tubular member and releasably connected to the body member. The body member includes an annular groove, and the safety device comprises locking elements. When the needle is retracted from the catheter assembly after puncturing the vein of a patient, the body member is disengaged by disengaging the locking elements from the annular groove, thereby separating the safety device from the body member after the needle has been arrested within safety device. The locking elements are solid spherical elements of stainless steel material.

9 Claims, 10 Drawing Sheets

(56) References Cited

U.S. PATENT DOCUMENTS

| | | |
|---|---|---|
| 4,778,453 A | 10/1988 | Lopez |
| 4,832,696 A | 5/1989 | Luther et al. |
| 4,834,718 A | 5/1989 | McDonald |
| 4,846,805 A | 6/1989 | Sitar |
| 4,878,902 A | 11/1989 | Wanderer |
| 4,887,998 A | 12/1989 | Martin et al. |
| 4,897,083 A | 1/1990 | Martell |
| 4,917,668 A | 4/1990 | Haindl |
| 4,929,241 A | 5/1990 | Kulli |
| 4,932,940 A | 6/1990 | Walker et al. |
| 4,944,725 A | 7/1990 | McDonald |
| 4,944,728 A | 7/1990 | Carrell et al. |
| 4,950,252 A | 8/1990 | Luther et al. |
| 4,952,207 A | 8/1990 | Lemieux |
| 4,964,854 A | 10/1990 | Luther |
| 5,000,740 A | 3/1991 | Ducharme et al. |
| 5,002,536 A | 3/1991 | Thompson et al. |
| 5,013,304 A | 5/1991 | Russell et al. |
| 5,030,205 A | 7/1991 | Holdaway et al. |
| 5,078,694 A | 1/1992 | Wallace |
| 5,092,845 A | 3/1992 | Chang |
| 5,098,410 A | 3/1992 | Kerby et al. |
| 5,108,379 A | 4/1992 | Dolgin et al. |
| 5,120,319 A | 6/1992 | Van Heugten |
| 5,135,504 A | 8/1992 | McLees |
| 5,156,599 A | 10/1992 | Ranford et al. |
| 5,195,974 A | 3/1993 | Hardy |
| 5,195,992 A | 3/1993 | Dudar et al. |
| 5,205,829 A | 4/1993 | Lituchy |
| 5,215,525 A | 6/1993 | Sturman |
| 5,215,528 A | 6/1993 | Purdy et al. |
| RE34,416 E | 10/1993 | Lemieux |
| 5,300,045 A | 4/1994 | Plassche |
| 5,322,517 A | 6/1994 | Sircom et al. |
| 5,328,482 A | 7/1994 | Sircom et al. |
| 5,334,158 A | 8/1994 | McLees |
| 5,344,408 A | 9/1994 | Partika |
| 5,409,461 A | 4/1995 | Steinman |
| 5,419,766 A | 5/1995 | Chang et al. |
| 5,423,766 A | 6/1995 | Cesare |
| 5,533,974 A | 7/1996 | Gaba |
| 5,558,651 A | 9/1996 | Crawford et al. |
| 5,562,631 A | 10/1996 | Bogart |
| 5,599,310 A | 2/1997 | Bogert |
| 5,601,532 A | 2/1997 | Gaba |
| 5,601,535 A | 2/1997 | Byrne et al. |
| 5,601,536 A | 2/1997 | Crawford et al. |
| 5,611,781 A | 3/1997 | Sircom et al. |
| 5,662,610 A | 9/1997 | Sircom |
| 5,676,658 A | 10/1997 | Erskine |
| 5,688,249 A | 11/1997 | Chang et al. |
| 5,690,619 A | 11/1997 | Erskine |
| 5,695,474 A | 12/1997 | Daugherty |
| 5,697,907 A | 12/1997 | Gaba |
| 5,702,367 A | 12/1997 | Cover et al. |
| 5,713,876 A | 2/1998 | Bogert et al. |
| 5,800,395 A | 9/1998 | Botich et al. |
| 5,810,785 A | 9/1998 | Bogert et al. |
| 5,830,189 A | 11/1998 | Chang |
| 5,853,393 A | 12/1998 | Bogert |
| 5,879,337 A | 3/1999 | Kuracina et al. |
| 5,911,705 A | 6/1999 | Howell |
| 6,004,294 A | 12/1999 | Brimhall et al. |
| 6,050,976 A | 4/2000 | Thorne et al. |
| 6,077,244 A | 6/2000 | Botich et al. |
| 6,117,108 A | 9/2000 | Woehr et al. |
| 6,203,527 B1 | 3/2001 | Zadini et al. |
| 6,221,047 B1 | 4/2001 | Greene et al. |
| 6,280,419 B1 | 8/2001 | Vojtasek |
| 6,287,278 B1 | 9/2001 | Woehr et al. |
| 6,287,317 B1 | 9/2001 | Makower et al. |
| 6,379,337 B1 | 4/2002 | Mohammad |
| 6,443,929 B1 | 9/2002 | Kuracina et al. |
| 6,461,362 B1 | 10/2002 | Halseth et al. |
| 6,491,707 B2 | 12/2002 | Makower et al. |
| 6,533,759 B1 | 3/2003 | Watson et al. |
| 6,582,402 B1 | 6/2003 | Erskine |
| 6,595,954 B1 | 7/2003 | Luther et al. |
| 6,595,955 B2 | 7/2003 | Ferguson et al. |
| 6,616,630 B1 | 9/2003 | Woehr et al. |
| 6,620,136 B1 | 9/2003 | Pressly et al. |
| 6,623,458 B2 | 9/2003 | Woehr et al. |
| 6,629,957 B1 | 10/2003 | Wiklund |
| 6,629,959 B2 | 10/2003 | Kuracina et al. |
| 6,652,490 B2 | 11/2003 | Howell |
| 6,689,102 B2 | 2/2004 | Greene |
| D491,266 S | 6/2004 | Cindrich et al. |
| 6,749,588 B1 | 6/2004 | Cindrich et al. |
| 6,796,962 B2 | 9/2004 | Ferguson et al. |
| 6,860,871 B2 | 3/2005 | Kuracina et al. |
| 6,872,193 B2 | 3/2005 | Shaw et al. |
| 6,893,423 B2 | 5/2005 | Denolly |
| 6,902,546 B2 | 6/2005 | Ferguson |
| 6,942,652 B1 | 9/2005 | Pressly et al. |
| 6,972,002 B2 | 12/2005 | Thorne |
| 6,979,333 B2 | 12/2005 | Hammerslag |
| 6,981,965 B2 | 1/2006 | Luther et al. |
| 6,995,814 B2 | 2/2006 | Kanatsu |
| 7,014,622 B1 | 3/2006 | Pressly et al. |
| 7,037,292 B2 | 5/2006 | Carlyon et al. |
| 7,179,244 B2 | 2/2007 | Smith et al. |
| 7,186,239 B2 | 3/2007 | Woehr |
| 7,255,685 B2 | 8/2007 | Pressly, Sr. et al. |
| 7,264,613 B2 | 9/2007 | Woehr et al. |
| 7,303,547 B2 | 12/2007 | Pressly et al. |
| 7,341,573 B2 | 3/2008 | Ferguson et al. |
| 7,344,516 B2 | 3/2008 | Erskine |
| 7,347,853 B2 | 3/2008 | DiFiore et al. |
| 7,413,562 B2 | 8/2008 | Ferguson et al. |
| 7,500,965 B2 | 3/2009 | Menzi et al. |
| D592,302 S | 5/2009 | Stokes et al. |
| 7,534,227 B2 | 5/2009 | Kulli |
| 7,604,616 B2 | 10/2009 | Thoresen et al. |
| 7,611,499 B2 | 11/2009 | Woehr et al. |
| 7,625,360 B2 | 12/2009 | Woehr et al. |
| 7,632,243 B2 | 12/2009 | Bialecki et al. |
| 7,658,725 B2 | 2/2010 | Bialecki et al. |
| 7,678,080 B2 | 3/2010 | Shue et al. |
| 7,699,807 B2 | 4/2010 | Faust et al. |
| 7,736,342 B2 | 6/2010 | Abriles et al. |
| 7,753,877 B2 | 7/2010 | Bialecki et al. |
| 7,753,887 B2 | 7/2010 | Botich et al. |
| 7,785,296 B2 | 8/2010 | Muskatello et al. |
| 7,828,774 B2 | 11/2010 | Harding et al. |
| 7,951,121 B2 | 5/2011 | Weaver et al. |
| 7,963,948 B2 | 6/2011 | Melsheimer |
| 7,972,313 B2 | 7/2011 | Woehr et al. |
| 8,062,252 B2 | 11/2011 | Alheidt et al. |
| 8,070,725 B2 | 12/2011 | Christensen |
| 8,105,288 B2 | 1/2012 | Keyser et al. |
| 8,133,206 B2 | 3/2012 | Greene et al. |
| 8,172,805 B2 | 5/2012 | Mogensen et al. |
| 8,211,070 B2 | 7/2012 | Woehr et al. |
| 8,235,946 B2 | 8/2012 | Molgaard-Nielsen |
| 8,251,950 B2 | 8/2012 | Albert et al. |
| 8,257,322 B2 | 9/2012 | Koehler et al. |
| 8,282,605 B2 | 10/2012 | Tan et al. |
| 8,308,685 B2 | 11/2012 | Botich et al. |
| 8,308,691 B2 | 11/2012 | Woehr et al. |
| 8,328,762 B2 | 12/2012 | Woehr et al. |
| 8,333,735 B2 | 12/2012 | Woehr et al. |
| 8,337,463 B2 | 12/2012 | Woehr et al. |
| 8,377,040 B2 | 2/2013 | Burkholz et al. |
| 8,382,721 B2 | 2/2013 | Woehr et al. |
| 8,398,597 B2 | 3/2013 | Brimhall |
| 8,403,886 B2 | 3/2013 | Bialecki et al. |
| 8,454,574 B2 | 6/2013 | Weaver et al. |
| 8,454,579 B2 | 6/2013 | Fangrow |
| 8,460,247 B2 | 6/2013 | Woehr et al. |
| 8,540,728 B2 | 9/2013 | Woehr et al. |
| 8,568,372 B2 | 10/2013 | Woehr et al. |
| 8,585,660 B2 | 11/2013 | Murphy |
| 8,591,469 B2 | 11/2013 | Keyser et al. |
| 8,597,249 B2 | 12/2013 | Woehr et al. |

(56) References Cited

U.S. PATENT DOCUMENTS

| | | |
|---|---|---|
| 8,603,009 B2 | 12/2013 | Tan et al. |
| 8,647,301 B2 | 2/2014 | Bialecki et al. |
| 8,647,313 B2 | 2/2014 | Woehr et al. |
| 8,771,230 B2 | 7/2014 | White et al. |
| 8,784,386 B2 | 7/2014 | Baid |
| 8,795,198 B2 | 8/2014 | Tan et al. |
| 8,814,833 B2 | 8/2014 | Farrell et al. |
| D713,522 S | 9/2014 | Woehr et al. |
| D713,957 S | 9/2014 | Woehr et al. |
| 8,827,965 B2 | 9/2014 | Woehr et al. |
| 8,834,422 B2 | 9/2014 | Walker et al. |
| 8,845,584 B2 | 9/2014 | Ferguson et al. |
| 8,882,742 B2 | 11/2014 | Dikeman et al. |
| 8,936,575 B2 | 1/2015 | Moulton |
| 9,033,927 B2 | 5/2015 | Maan et al. |
| 9,095,683 B2 | 8/2015 | Hall et al. |
| 9,149,626 B2 | 10/2015 | Woehr et al. |
| 9,174,036 B2 | 11/2015 | Okamura et al. |
| 9,180,277 B2 | 11/2015 | Erskine |
| 9,186,455 B2 | 11/2015 | Moyer |
| 9,278,195 B2 | 3/2016 | Erskine |
| 9,289,237 B2 | 3/2016 | Woehr et al. |
| 9,314,608 B2 | 4/2016 | Weaver et al. |
| 9,320,870 B2 | 4/2016 | Woehr |
| 9,370,641 B2 | 6/2016 | Woehr et al. |
| 9,402,964 B2 | 8/2016 | Crawford |
| 9,427,549 B2 | 8/2016 | Woehr et al. |
| 9,504,786 B2 | 11/2016 | Carlyon et al. |
| 9,555,220 B2 | 1/2017 | Koehler et al. |
| 9,555,221 B2 | 1/2017 | Koehler et al. |
| 9,604,035 B2 | 3/2017 | Keyser et al. |
| 9,623,210 B2 | 4/2017 | Woehr |
| 9,764,085 B2 | 9/2017 | Teoh |
| 9,775,972 B2 | 10/2017 | Christensen et al. |
| 9,775,973 B2 | 10/2017 | Keyser et al. |
| 9,782,546 B2 | 10/2017 | Woehr |
| 9,827,398 B2 | 11/2017 | White et al. |
| 9,844,646 B2 | 12/2017 | Knutsson |
| 9,844,648 B2 | 12/2017 | Nakajima et al. |
| 9,933,079 B2 | 4/2018 | Weaver et al. |
| 9,962,525 B2 | 5/2018 | Woehr |
| 10,028,691 B2 | 7/2018 | Goral et al. |
| 10,052,474 B2 | 8/2018 | Keyser et al. |
| 10,080,869 B2 | 9/2018 | Woehr et al. |
| 10,307,571 B2 | 6/2019 | Burkholz |
| 10,314,984 B2 | 6/2019 | Koehler et al. |
| 10,406,327 B2 | 9/2019 | Holm et al. |
| 10,449,331 B2 | 10/2019 | Lim et al. |
| 10,456,572 B2 | 10/2019 | Woehr |
| 10,500,375 B2 | 12/2019 | Isaacson et al. |
| 10,500,376 B2 | 12/2019 | Isaacson et al. |
| 10,548,522 B2 | 2/2020 | Akcay et al. |
| 10,589,081 B2 | 3/2020 | Servin De La Mora Godinez et al. |
| 10,596,351 B2 | 3/2020 | Liska |
| 10,625,067 B2 | 4/2020 | Al-Ali |
| 10,661,058 B2 | 5/2020 | Woehr |
| 10,675,440 B2 | 6/2020 | Abitabilo et al. |
| 10,682,499 B2 | 6/2020 | Isaacson et al. |
| 10,695,551 B2 | 6/2020 | Shevgoor et al. |
| 10,835,729 B2 | 11/2020 | Agrawal et al. |
| 10,850,068 B2 | 12/2020 | Teoh |
| 11,071,849 B2 | 7/2021 | Ng et al. |
| 2002/0161386 A1 | 10/2002 | Halseth et al. |
| 2002/0165497 A1 | 11/2002 | Greene |
| 2002/0169418 A1 | 11/2002 | Menzi et al. |
| 2003/0060760 A1 | 3/2003 | Botich et al. |
| 2003/0083620 A1 | 5/2003 | Luther et al. |
| 2003/0100868 A1 | 5/2003 | Ferguson et al. |
| 2003/0199827 A1 | 10/2003 | Thorne |
| 2004/0049155 A1 | 3/2004 | Schramm |
| 2004/0059296 A1 | 3/2004 | Godfrey |
| 2004/0078003 A1 | 4/2004 | Smith et al. |
| 2004/0127854 A1 | 7/2004 | Leinsing et al. |
| 2004/0158208 A1 | 8/2004 | Hiejima |
| 2004/0168690 A1 | 9/2004 | Payne |
| 2004/0186434 A1 | 9/2004 | Harding et al. |
| 2004/0204681 A1 | 10/2004 | Thoresen et al. |
| 2004/0236288 A1 | 11/2004 | Howell et al. |
| 2004/0267204 A1 | 12/2004 | Brustowicz |
| 2005/0038384 A1 | 2/2005 | Li |
| 2005/0096592 A1 | 5/2005 | Carlyon et al. |
| 2005/0113755 A1 | 5/2005 | Greene et al. |
| 2005/0277879 A1 | 12/2005 | Daga |
| 2006/0036219 A1 | 2/2006 | Alvin |
| 2006/0041231 A1 | 2/2006 | Pressly et al. |
| 2006/0229556 A1 | 10/2006 | Pressly et al. |
| 2007/0191776 A1 | 8/2007 | Bialecki et al. |
| 2008/0097330 A1 | 4/2008 | King et al. |
| 2008/0119795 A1* | 5/2008 | Erskine ............ A61M 25/0618 604/263 |
| 2008/0228150 A1 | 9/2008 | Jones et al. |
| 2009/0137958 A1 | 5/2009 | Erskine |
| 2009/0209912 A1 | 8/2009 | Keyser et al. |
| 2009/0222003 A1 | 9/2009 | Otley |
| 2009/0312711 A1 | 12/2009 | Brimhall |
| 2010/0042048 A1 | 2/2010 | Christensen |
| 2010/0241087 A1 | 9/2010 | Moulton |
| 2011/0015573 A1 | 1/2011 | Maan et al. |
| 2011/0301551 A1 | 12/2011 | Koehler et al. |
| 2011/0306933 A1 | 12/2011 | Djordejevic et al. |
| 2011/0319825 A1 | 12/2011 | Goral et al. |
| 2012/0035552 A1 | 2/2012 | Woehr |
| 2012/0089101 A1 | 4/2012 | Carlyon et al. |
| 2012/0150118 A1 | 6/2012 | Keyser et al. |
| 2013/0030391 A1 | 1/2013 | Baid |
| 2013/0165868 A1 | 6/2013 | Isaacson et al. |
| 2013/0237928 A1* | 9/2013 | Fisher ............... A61M 25/0625 604/263 |
| 2014/0025009 A1 | 1/2014 | Erskine |
| 2014/0052022 A1 | 2/2014 | Tan et al. |
| 2014/0058357 A1 | 2/2014 | Keyser et al. |
| 2014/0200549 A1 | 7/2014 | Norkunas |
| 2014/0236099 A1 | 8/2014 | Nakagami et al. |
| 2014/0336582 A1 | 11/2014 | Tisci |
| 2014/0365809 A1 | 12/2014 | Higeta et al. |
| 2014/0371715 A1 | 12/2014 | Farrell et al. |
| 2015/0094751 A1 | 4/2015 | Chen et al. |
| 2015/0224267 A1 | 8/2015 | Farrell et al. |
| 2015/0265827 A1 | 9/2015 | Keyser et al. |
| 2015/0328438 A1 | 11/2015 | Baid |
| 2016/0008581 A1 | 1/2016 | Ang et al. |
| 2016/0175563 A1 | 6/2016 | Woehr et al. |
| 2016/0175576 A1 | 6/2016 | Neff et al. |
| 2016/0220161 A1 | 8/2016 | Goral et al. |
| 2016/0220791 A1 | 8/2016 | Akcay et al. |
| 2016/0271370 A1 | 9/2016 | Keyser et al. |
| 2016/0331935 A1 | 11/2016 | Saatchi et al. |
| 2016/0361490 A1 | 12/2016 | Phang et al. |
| 2016/0361519 A1 | 12/2016 | Teoh et al. |
| 2016/0374685 A1 | 12/2016 | Abbott et al. |
| 2017/0035992 A1 | 2/2017 | Harding et al. |
| 2017/0035995 A1 | 2/2017 | Shevgoor et al. |
| 2017/0043134 A1 | 2/2017 | Harding et al. |
| 2017/0120011 A1 | 5/2017 | Burkholz et al. |
| 2017/0120017 A1 | 5/2017 | Burkholz et al. |
| 2017/0274183 A1 | 9/2017 | Burkholz et al. |
| 2017/0319822 A1 | 11/2017 | Ang |
| 2017/0333642 A1 | 11/2017 | Shevgoor et al. |
| 2017/0361070 A1 | 12/2017 | Hivert |
| 2018/0064912 A1 | 3/2018 | Keyser et al. |
| 2018/0078741 A1 | 3/2018 | Stokes |
| 2018/0154119 A1 | 6/2018 | White et al. |
| 2018/0214673 A1 | 8/2018 | Ng et al. |
| 2018/0214682 A1 | 8/2018 | Woehr et al. |
| 2018/0256885 A1 | 9/2018 | Shevgoor et al. |
| 2018/0289932 A1 | 10/2018 | Isaacson et al. |
| 2018/0296149 A1 | 10/2018 | Goral et al. |
| 2018/0304048 A1 | 10/2018 | Knutsson |
| 2018/0311475 A1 | 11/2018 | Baid |
| 2018/0361119 A1 | 12/2018 | Goral et al. |
| 2019/0160264 A1 | 5/2019 | Isaacson |
| 2019/0262549 A1 | 8/2019 | Koehler et al. |
| 2019/0351210 A1 | 11/2019 | Solomon et al. |

(56) References Cited

U.S. PATENT DOCUMENTS

| | | |
|---|---|---|
| 2020/0094026 A1 | 3/2020 | Isaacson et al. |
| 2020/0094037 A1 | 3/2020 | Tran et al. |
| 2020/0121896 A1 | 4/2020 | Baid |
| 2020/0146605 A1 | 5/2020 | Paliwoda |
| 2020/0155808 A1 | 5/2020 | Burkholz et al. |
| 2020/0188634 A1 | 6/2020 | Woehr et al. |
| 2020/0197667 A1 | 6/2020 | Gupta |
| 2020/0261702 A1 | 8/2020 | Jewell et al. |
| 2021/0187249 A1 | 6/2021 | Lagana et al. |
| 2021/0308427 A1 | 10/2021 | Ng et al. |
| 2021/0370020 A1 | 12/2021 | Gupta |
| 2021/0402143 A1 | 12/2021 | Yokota et al. |
| 2022/0249810 A1 | 8/2022 | Gupta |

FOREIGN PATENT DOCUMENTS

| | | |
|---|---|---|
| CA | 2033361 C | 11/2002 |
| CA | 2710969 A1 | 7/2009 |
| CN | 106659438 A | 5/2017 |
| CN | 107427633 A | 12/2017 |
| DE | 4442352 C1 | 12/1995 |
| EP | 0747083 A2 | 12/1996 |
| EP | 0747085 A2 | 12/1996 |
| EP | 0750916 A2 | 1/1997 |
| EP | 3209363 B1 | 3/2019 |
| EP | 3622992 A1 | 3/2020 |
| EP | 3622999 A1 | 3/2020 |
| IN | 201911036272 | 1/2020 |
| JP | 07024071 A | 1/1995 |
| JP | 2001046507 A | 2/2001 |
| JP | 2001190683 A | 7/2001 |
| JP | 20041544364 A | 6/2004 |
| JP | 2022551563 A | 12/2022 |
| WO | 9308865 A1 | 5/1993 |
| WO | 9413341 A1 | 6/1994 |
| WO | 0168174 A2 | 9/2001 |
| WO | 2007061718 A2 | 5/2007 |
| WO | 2007098355 A1 | 8/2007 |
| WO | 2010107645 A1 | 9/2010 |
| WO | 2011152916 A1 | 12/2011 |
| WO | 2013051242 A1 | 4/2013 |
| WO | 2015161294 A1 | 10/2015 |
| WO | 2016033143 A1 | 3/2016 |
| WO | 2016063287 A1 | 4/2016 |
| WO | 2016135293 A2 | 9/2016 |
| WO | 2017042825 A2 | 3/2017 |
| WO | 2018096549 A1 | 5/2018 |
| WO | 2018217781 A1 | 11/2018 |
| WO | 2019008432 A1 | 1/2019 |
| WO | 2019152630 A1 | 8/2019 |
| WO | 2020011663 A1 | 1/2020 |
| WO | 2020120404 A1 | 6/2020 |
| WO | 2020127328 A1 | 6/2020 |
| WO | 2020189466 A1 | 9/2020 |
| WO | 2021048867 A1 | 3/2021 |
| WO | 2023137377 A1 | 7/2023 |
| WO | 2023137380 A1 | 7/2023 |

OTHER PUBLICATIONS

International Search Report and Written Opinion issued in International Application No. PCT/US2023/060560, mailed on Jun. 2, 2023, 10 pages.
International Preliminary Report on Patentability issued in International Application No. PCT/US2022/016002, mailed on Aug. 24, 2023, 6 pages.
"PTFE—Polytetrafluoroethylene", Summary of Properties, Jul. 4, 2017, Zeus Inc.
International Search Report and Written Opinion dated Apr. 19, 2022 in connection with International Patent Application No. PCT/US2022/016002, 7 pages.
International Search Report and Written Opinion dated Jul. 20, 2022 in connection with International Patent Application No. PCT/US2022/027597, 9 pages.
International Search Report and Written Opinion for PCT Application No. PCT/IN2018/050178, Dated Jun. 12, 2018, 8 pages.
International Search Report and Written Opinion issued in International Application No. PCT/US2023/060554, mailed on May 9, 2023, 11 pages.
Extended European Search Report issued in European Patent Applicaiton No. 22753355.1, mailed on Dec. 13, 2024, 10 pages,.
First Examination Report issued in Indian Patent Application No. 201911036272, mailed on Feb. 10, 2020, 5 pages.
Hearing Notice issued in Indian patent Application No. 201911036272, mailed on Jul. 16, 2020, 2 pages.
International Preliminary Report on Patentability issued in International Application No. PCT/US2023/060554, mailed on Jul. 25, 2024, 10 pages.
International Preliminary Report on Patentability issued in International Patent Application No. PCT/US2023/060560, mailed on Jul. 25, 2024, 9 pages.
Extended European Search Report issued in European Patent Application No. 22799471.2, mailed on Feb. 13, 2025, 11 pages.
Office Action issued in Canadian Patent Application No. 3,169,051, mailed on Feb. 12, 2025, 4 pages.

* cited by examiner

SAFETY INTRAVENOUS CANNULA

CROSS-REFERENCE TO RELATED APPLICATION

This patent application claims the priority of Indian patent application number 202111020693, filed May 6, 2021 entitled "Safety Intravenous Cannula," the disclosure content of which is hereby incorporated by reference.

TECHNICAL FIELD

The present disclosure is related to a medical device, more particularly to a locking mechanism for an intravenous cannula which prevents needle stick injuries.

BACKGROUND OF THE DISCLOSURE

Intravenous catheters are typical medical devices used to obtain continuous vascular access in patients. These devices generally have a disposable hollow-bore needle, and over the needle, a catheter made up of plastic or a polymer material has been used to access a lumen of a blood vessel in a patient. The intravenous catheter is advanced into the blood vessel and is used for administering fluid like blood or liquid medication.

When a catheter is inserted into a patient's vein for the intravenous delivery of fluid, the disposable needle passing through the catheter is utilized to make a puncture to permit the entry of the tip of the catheter into the patient's vein. The needle is then withdrawn, leaving the catheter in place either for a direct hook up to a fluid bottle to be delivered, or to be closed/capped for later use.

The needle of cannulas presently being used by medical personnel may not have safety features which can prevent needle stick injuries that may be caused due to an accidental sticking before the used cannula is disposed of. The risks associated with such needle stick injuries are very high, because of high prevalence of communicable diseases among patients who reach hospitals and especially in emergency rooms of hospitals where cannulation treatment must be initiated immediately. The costs associated with such needle stick injuries are also very high.

Therefore, the present disclosure is directed to overcome one or more of the problems set forth above.

SUMMARY OF THE DISCLOSURE

The present disclosure provides for a safety intravenous cannula. The cannula comprises a catheter assembly comprising a catheter hub, the catheter hub having a distal end connected to a proximal end of a catheter tube, and a body member adapted to accommodate the catheter hub at a distal end of the body member. The cannula also includes an elongated tubular member disposed at a proximal end of the catheter assembly. A needle hub comprising a needle holder is disposed inside the elongated tubular member. A distal end of the needle holder is connected with a needle. A safety device is fixedly connected to a distal end of the elongated tubular member at a first end of the safety device and releasably connected to the body member of the catheter assembly at a second end of the safety device. The body member is provided with an annular groove at an inner surface of the body member. The safety device comprises one or more locking elements at the second end of the safety device. The one or more locking elements of the safety device are adapted to engage with the annular groove of the body member, thereby forming a locking engagement and a tight fit relationship between the elongated tubular member and the catheter assembly when the needle is passed through the safety device for puncturing a vein of a patient. When the needle is retracted from the catheter assembly after puncturing the vein of the patient, the body member which is in a tight fit relationship with the catheter assembly is disengaged by disengaging the locking elements from the annular groove, thereby disengaging the locking engagement between the elongated tubular member and the catheter assembly, and separating the safety device from the body member of the catheter assembly and the needle being adapted to be arrested within the safety device.

In an embodiment, the safety device comprises a groove on an outer surface of the safety device to accommodate one or more locking elements.

In an embodiment, the one or more locking elements are solid spherical elements made of stainless steel material.

In an embodiment, the groove of the safety device has a diameter more than or equal to a diameter of the solid spherical elements.

In an embodiment, the first end of the safety device has a circular base portion, the circular base portion fixedly connected with the distal end of the elongated tubular member and including a central hole.

In an embodiment, the safety device comprises a tubular portion extending from the circular base portion and includes an axial bore forming the passage for the needle from the central hole.

In an embodiment, the groove is provided on the outer surface of the tubular portion of the safety device extending towards the axial bore of the safety device.

In embodiments, the solid spherical elements of the safety device are adapted to extend outwardly to engage with the annular groove of the body member, thereby forming the locking engagement and the tight fit relationship between the elongated tubular member and the catheter assembly when the needle is passed through the safety device for puncturing the vein of the patient.

In embodiments, when the needle is retracted from the needle cover after puncturing the vein of the patient, the body member which is in a tight fit relationship with the catheter assembly is disengaged by disengaging the solid spherical elements from the annular groove, thereby disengaging the locking engagement between the elongated tubular member and the catheter assembly and separating the safety device from the body member of the catheter assembly and the needle being adapted to be arrested within the safety device.

Other features and aspects of this disclosure will be apparent from the following description and the accompanying drawings.

BRIEF DESCRIPTION OF ACCOMPANYING DRAWINGS

DETAILED DESCRIPTION OF THE DISCLOSURE

Figure 1:
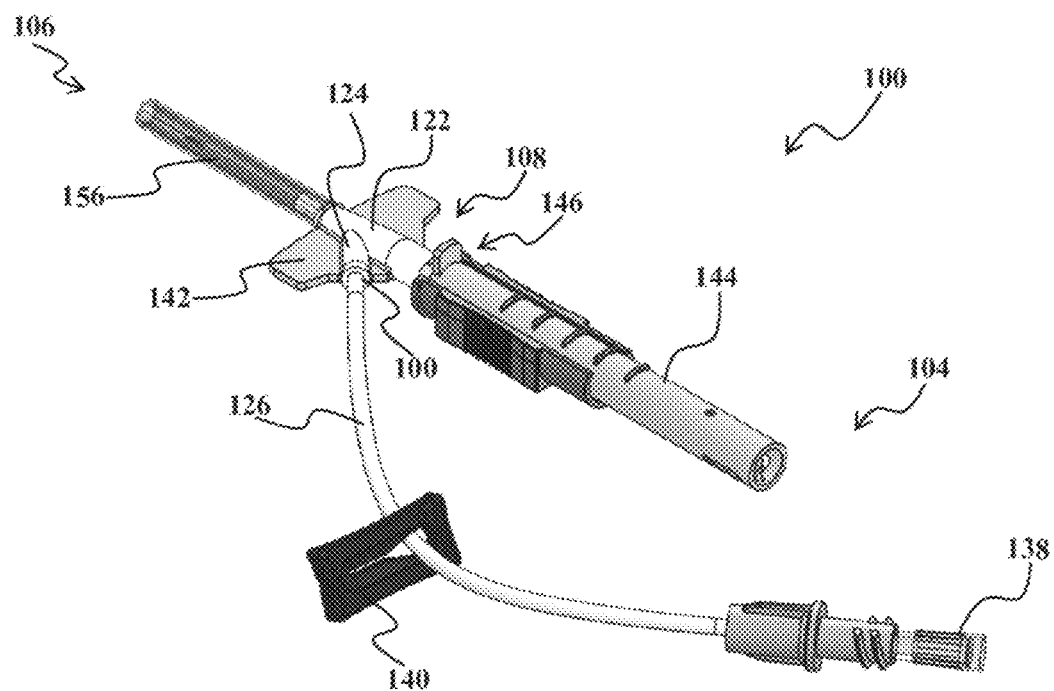
FIG. 1 shows a perspective view of a cannula having a safety device, according to a first exemplary embodiment of the present invention.

Provided below is a non-limiting exemplary embodiment of the present disclosure. Reference will now be made in detail to specific embodiments or features, examples of which are illustrated in the accompanying drawings. Wherever possible, corresponding or similar reference numbers will be used throughout the drawings to refer to the same or corresponding parts. Moreover, references to various elements described herein are made collectively or individually when there may be more than one element of the same type. However, such references are merely exemplary in nature. It may be noted that any reference to elements in the singular may also be construed to relate to the plural and vice-versa without limiting the scope of the disclosure to the exact number or type of such elements unless set forth explicitly in the appended claim.

The terms "distal or distal end" and "proximal or proximal end" as used, respectively in the present disclosure, refers to directions or ends which are farther away and closer, respectively, to the person administering a catheter into a body of a patient. The terms "connected" or "fixedly connected" as used in the present disclosure mean that the components can be attached to each other in a fixed manner so as to form a unison between them. The terms "releasably connected" imply that the components may be connected to each other, however, if the user desires, the connected elements may be disintegrated or separated from each other. The term "slidably connected" means that the components are assembled together in such a manner that any one or both of the components can be slid with respect to each other during working of the device. The contact surfaces of the components may enable sliding feature between the components. The term "disposed" as used herein means that the component/element of the device may be connected to another element in which the assembly forms a workable assembly, without hindering the working of the elements. The term "comprising" means that the device or components may include additional components apart from the components mentioned.

The disclosure may also include terms like, "one or more" or "at least", "a" or "an". It should be understood that the number mentioned should not limit the scope of the invention. In some examples, a single component may form a workable assembly, and in some other examples, "two or more" components may form a workable assembly. Such terms or limitation should not be considered to be limiting the scope of the invention. The skilled person may find or obtain multiple such combinations during regular permutation and combinations while bringing the invention to a workable model, and thereafter may find the device to be workable.

The disclosure may further include terms which may define shapes, like, "circular" or "cylindrical" or "converging" or "tapered" or "diverging" or "expanding". Again, such terminologies which define the shapes may be limiting to exemplary embodiments illustrated in the figures. It should not be meant that there are no other shapes possible. A person of ordinary skill in the art may come up with any other shape or combination of such shapes, which would lead to workability of the device. Therefore, any such alteration would still be covered in the disclosure without departing from the inventive step of the invention.

The terminology used in the present disclosure includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize and develop the invention.

FIG. 1 illustrates a perspective view of a cannula (100) comprising a safety device (102) (shown in FIG. 2), according to a first exemplary embodiment of the present invention. The cannula (100) is a medical device used on patients (not shown) undergoing a treatment for administration of a medication fluid or gases by an intravenous therapy or removal of body fluid for example 'blood sample', from the patients for a laboratory analysis. The terms "cannula" and "safety intravenous cannula" are interchangeably used in the present disclosure. It should be understood that the "cannula" and the "safety intravenous cannula" are one and the same. The term "cannula" may be used more often for sake of brevity.

Figure 2:
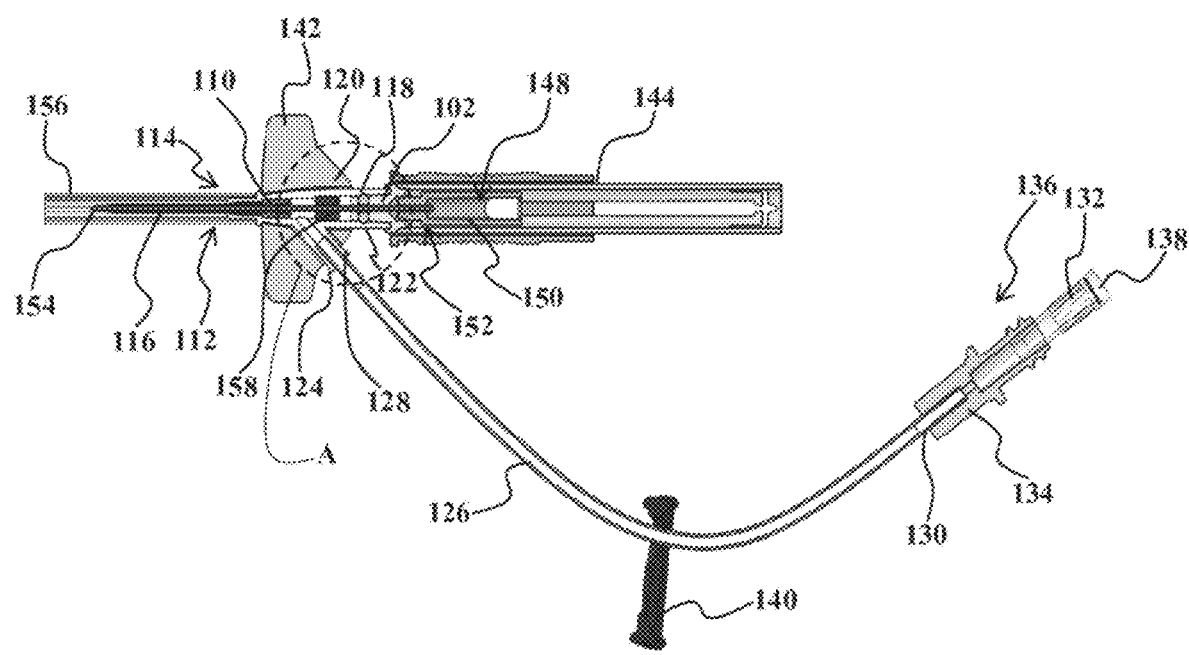
FIG. 2 shows a sectional view of the cannula shown in FIG. 1, where a needle is passed through a safety device for puncturing a vein.

In the illustrated FIGS. 1 and 2, the cannula (100) has a first end (104) closer to a user or an operator (not shown) and a second end (106) closer to the patient or a body part of the patient. The terms "user" or "operator" as used in the present disclosure may include, but are not limited to, medical personnel like nurses or paramedical staff who may work under a direction and supervision of doctors or physicians or surgeons. In the illustrated Figures, the cannula (100) comprises a catheter assembly (108) towards the second end (106) of the cannula (100). The catheter assembly (108) has a catheter hub (110) having a distal end (112) and is connected to a proximal end (114) of a catheter tube (116). The catheter assembly (108) further includes a body member (118) adapted to accommodate the catheter hub (110) at a distal end (120) of the body member (118).

The body member (118) in the illustrated exemplary embodiment is a Y-type body member. It is to be understood that the body member (118) may be of any other kind available in the market. The illustrated example of a Y-type body member is not limiting the scope of the present invention. A skilled person in the art may implement a suitable body member in the cannula for working of the cannula (100), and thus the specific example of a Y-type body member should not be construed as the only kind which can be implemented with the cannula (100) described in the present invention. The illustrated Y-type body member (118) has a cylindrical body portion (122) along the catheter hub (110) and a tangential portion (124) connected to the cylindrical body portion (122). Both the cylindrical body portion (122) and the tangential portion (124) are integrally formed or manufactured. In another embodiment, the tangential portion (124) may be releasably connected to the cylindrical body portion (122) of the body member (118). The fluids are as described above.

One end (128) of the tube (126) may be connected to the tangential portion (124) of the body member (118) and a second end (130) of the tube (126) may be connected to a flashback chamber (132). The flashback chamber (132) may include a female luer (134), a flow control hub (136) and a filter (138). The tube (126) may be further provided with a slide clamp (140) for arranging the tube (126) with a stand or supporting column (not shown). The cannula (100) is further provided with a wing member (142) around the body member (118). The wing member (142) may aid in connecting or affixing the catheter assembly (108) with the patient's body part like a hand after puncturing the vein.

Figure 8:
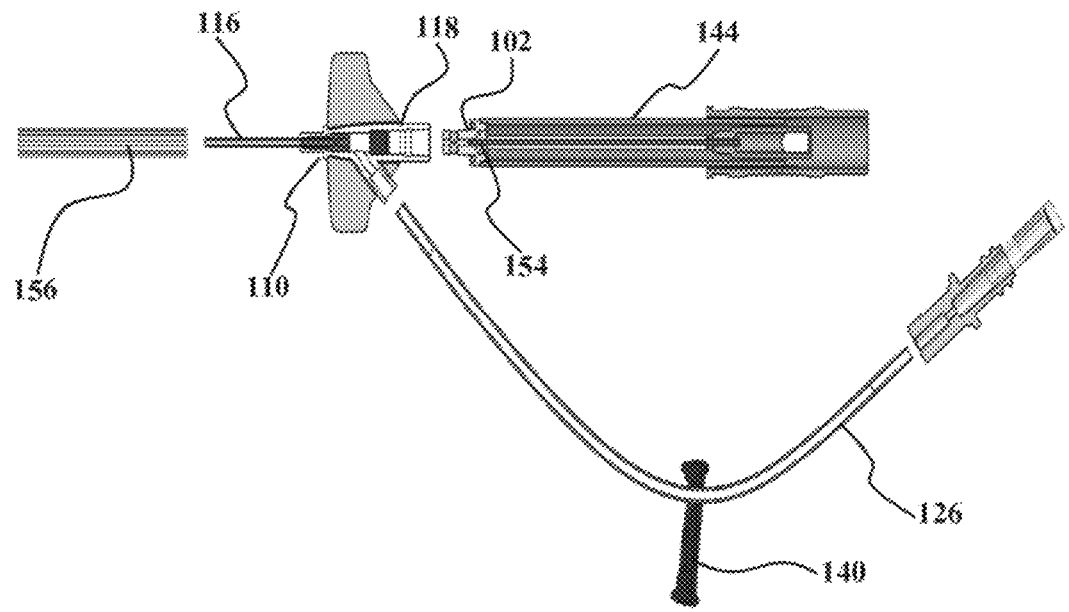
FIG. 8 shows a sectional view of the cannula, where the safety device is separated from a body member of the catheter assembly and the needle is arrested within the safety device.

The safety intravenous cannula (100) further comprises an elongated tubular member (144). The elongated tubular member (144) is disposed at a proximal end (146) of the catheter assembly (108). The cannula (100) further comprises a needle hub (148) comprising a needle holder (150). The needle holder (150) is disposed inside the elongated tubular member (144), wherein a distal end (152) of the needle holder (150) is connected with a needle (154). In the illustrated FIGS. 1 and 2, a needle protector (156) (more clearly shown in FIGS. 6 and 8) is provided covering the needle (154).

Figure 3:
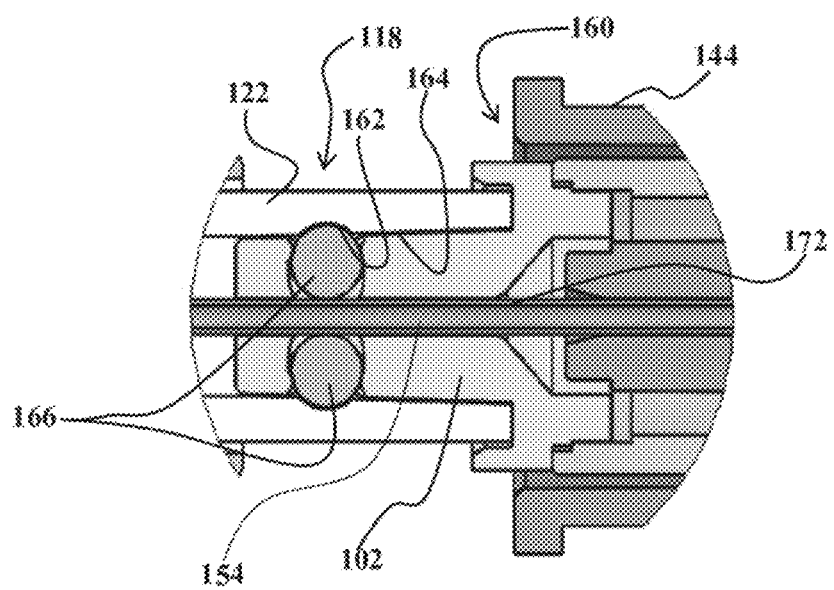
FIG. 3 shows a magnified view of portion "A" indicated in FIG. 2.

FIG. 2 illustrates a sectional view of the cannula (100) shown in FIG. 1. In this illustration, the needle (154) is passed through the safety device (102) according to the first exemplary embodiment of the present invention. After passing the safety device (102), the needle (154) passes through a rubber valve (158) disposed inside the body member (118), the catheter hub (110) and the catheter tube (116) for puncturing the vein. The safety device (102) is fixedly connected to a distal end (160) of the elongated tubular member (144) and releasably connected to the body member (118) of the catheter assembly (108) at an end opposite to the distal end (160) (more clearly shown in FIG. 3). In FIGS. 2 and 3 it is illustrated that the needle (154) is passed through the safety device (102) for puncturing the vein of the patient. FIG. 3 illustrates a magnified view of portion "A" indicated in FIG. 2. It is illustrated that the safety device (102) is provided between the body member (118) of the catheter assembly (108) and the elongated tubular member (144). The cylindrical body portion (122) of the body member (118) includes an annular groove (162) at an inner surface (164) of the body member (118). The annular groove (162) in the body member (118) is adapted to engage with one or more locking elements (166) of the safety device (102) when the needle (154) is passed through the safety device (102). In the illustrated figure, the locking elements (166) are solid spherical elements.

Figure 4:
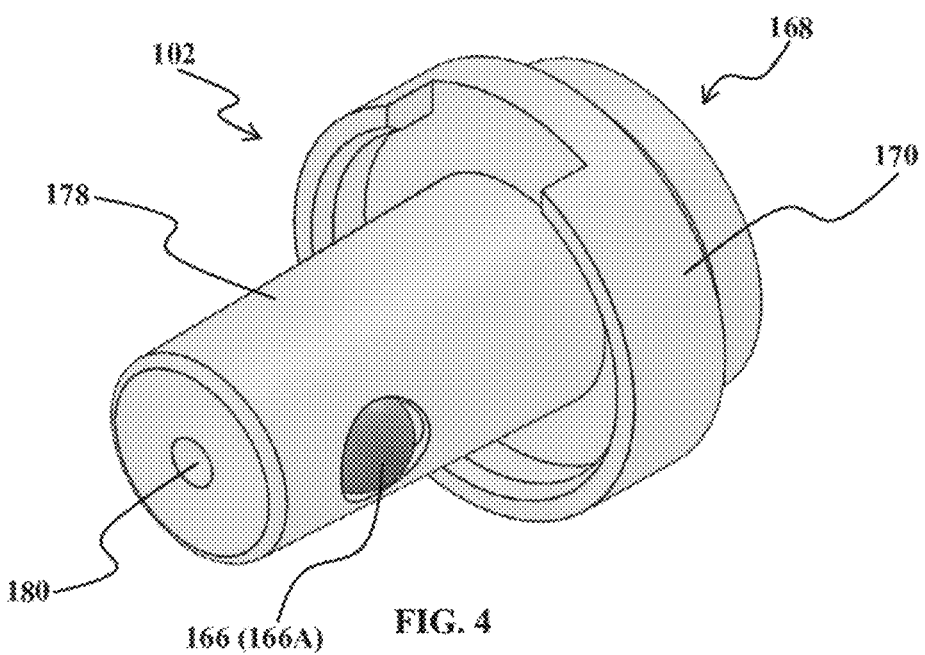
FIG. 4 shows a perspective view of the safety device shown in FIGS. 2-3, according to the first exemplary embodiment of the present invention.
Figure 5:
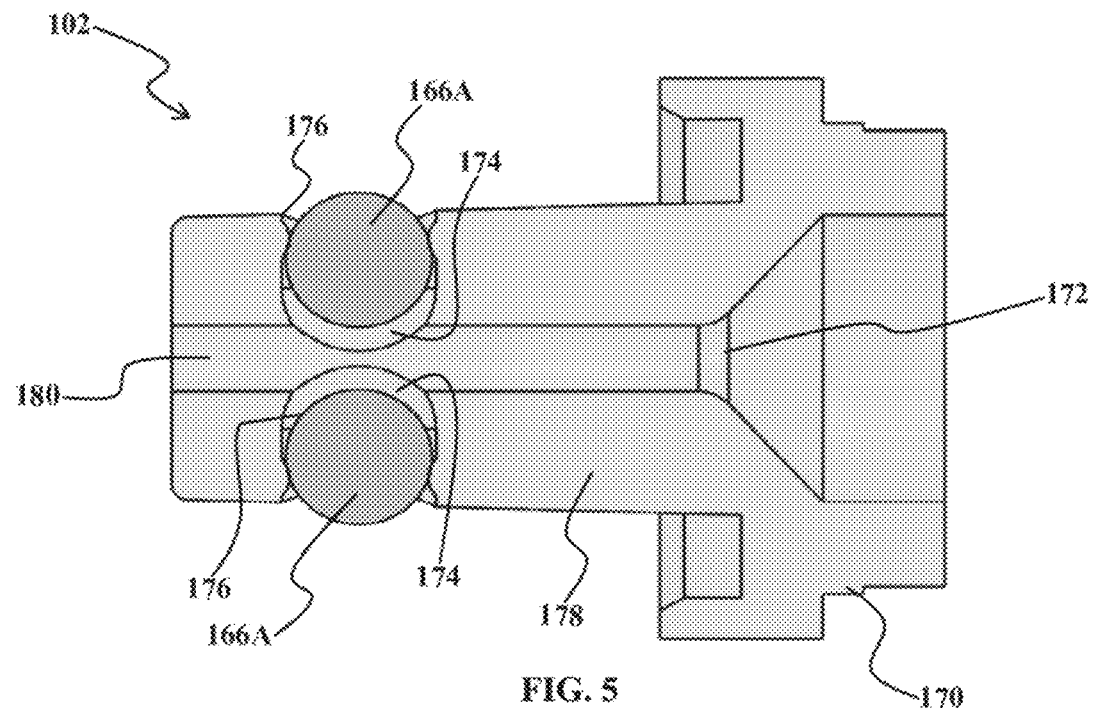
FIG. 5 shows a sectional view of the safety device shown in FIG. 4.

FIGS. 4 and 5 illustrate a perspective view and a sectional view of the safety device (102), respectively, according to the first exemplary embodiment of the present invention. The safety device (102) comprises a first end (168) having a circular base portion (170). The circular base portion (170) is fixedly connected with the distal end (160) of the elongated tubular member (144) (shown in FIGS. 2 and 3). In an exemplary embodiment, the circular base portion (170) of the safety device (102) is press-fitted to the elongated tubular member (144) forming a unison between the safety device (102) and the elongated tubular member (144). The circular base portion (170) is provided with a central hole (172) (shown in FIG. 5) for passage of the needle (154). The safety device (102) comprises one or more grooves (174) (shown in FIG. 5) on an outer surface (176) to accommodate the one or more locking elements (166). In the illustrated embodiment, the safety device (102) comprises a tubular portion (178) extending from the circular base portion (170) and includes an axial bore (180) forming the passage for the needle (154) from the central hole (172). The one or more grooves (174) are provided on the outer surface (176) of the tubular portion (178)/the safety device (102) and extend towards the axial bore (180) of the safety device (102). In the illustrated exemplary embodiment, there are two grooves (174) (clearly shown in FIG. 5) to accommodate the two locking elements (166).

In the illustrated figures, the two locking elements (166) are solid spherical elements. The solid spherical elements may be in the form of solid balls made of stainless steel material. It may be understood that the solid spherical elements (166A) may be made of any other materials which are bio-compatible or non-reactive to the fluids passing through the cannula.

The grooves (174) made on the outer surface (176) of the safety device (102) have substantially the same diameter as that of a diameter of the solid spherical elements (166A), or the grooves (174) of the safety device (102, 102A) may have a diameter greater than a diameter of the solid spherical elements (166A). This facilitates easy or smooth movement of the spherical balls outwardly when the needle (154) is passed through the axial bore (180) while puncturing the vein or withdrawn after puncturing the vein. In another exemplary embodiment, the diameter of the each groove (174) may be less or more that the diameter of the solid spherical elements. However, the diameters should be kept in such a manner that the movement of the spherical balls should not be hindered.

In the illustrated embodiments of FIGS. 2 and 3, the locking elements (166) or the solid balls of the safety device (102) are adapted to engage with the annular groove (162) of the body member (118). This forms a locking engagement and a tight fit relationship between the elongated tubular member (144) and the catheter assembly (108) when the needle (154) is passed through the safety device (102) for puncturing the vein of the patient.

Figure 6:
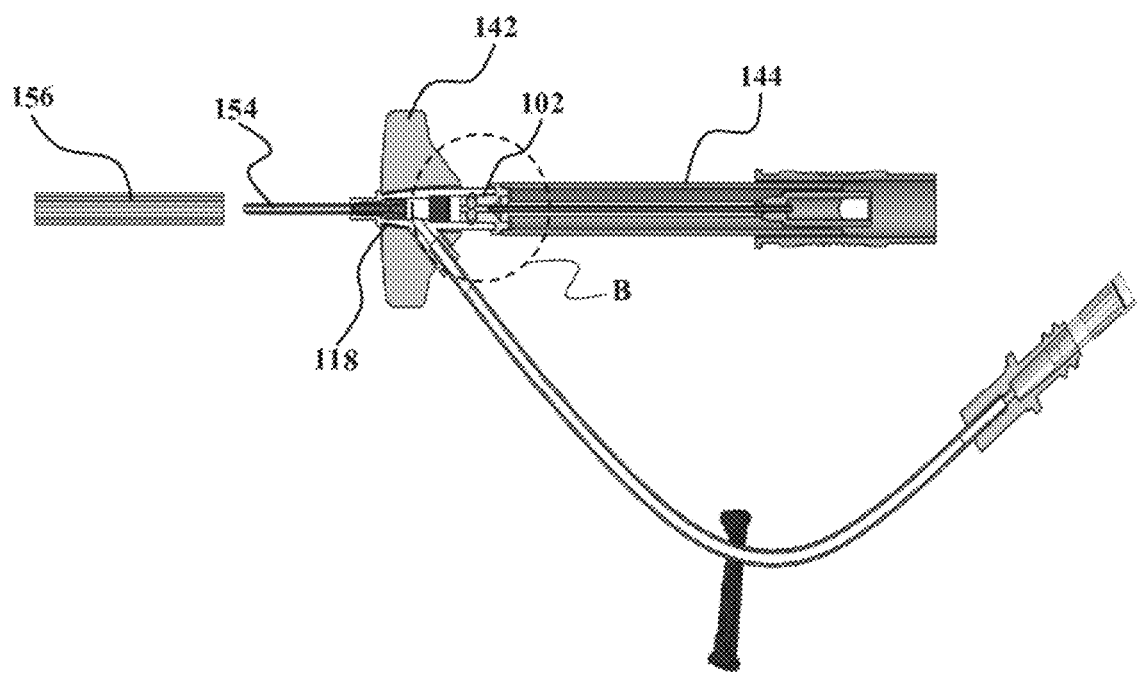
FIG. 6 shows a sectional view of the cannula, where a needle is withdrawn from the catheter assembly after puncturing the vein and a tip of the needle is arrested within the safety device.
Figure 7:
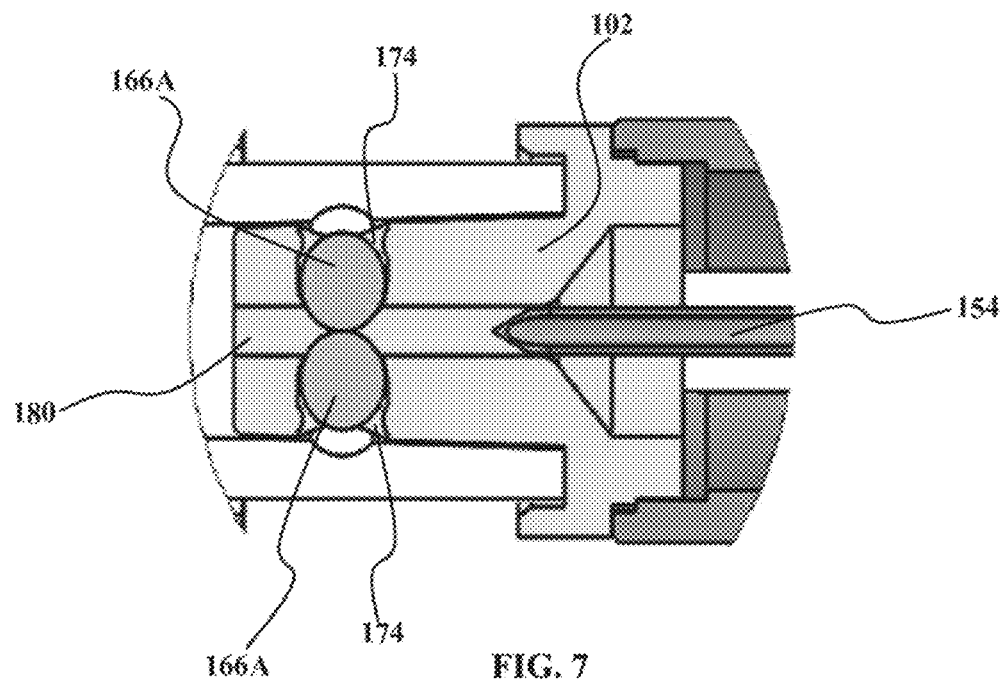
FIG. 7 shows a magnified view of portion "B" indicated in FIG. 6.

FIG. 6 illustrates a sectional view of the cannula (100) shown in FIGS. 1 and 2, where the needle (154) is withdrawn from the catheter assembly (108) after puncturing the vein and a tip or bevel (154A) of the needle (154) is arrested within the safety device (102). FIG. 7 shows a magnified view of portion "B" indicated in FIG. 6, where the tip or bevel (154A) of the needle (154) is arrested or accommodate in the safety device (102).

In the illustrated FIGS. 6 and 7, when the needle (154) is retracted from the catheter assembly (108) after puncturing the vein of the patient, the body member (118) which is in a tight fit relationship with the catheter assembly (108) is disengaged. The disengagement occurs because the locking elements (solid balls) (166A) are disengaged or displaced from the annular groove (162) of the body member (118), thereby disengaging the locking engagement between the elongated tubular member (144) and the catheter assembly (108), and separating the safety device (102) from the body member (118) of the catheter assembly (108). The separation of the safety device (102) from the body member (118) of the catheter assembly (108) (also shown in FIG. 8) arrests the needle (154) within the safety device (102). Thus, when the needle (154) is withdrawn after puncturing the vein, the needle tip or the bevel (154A) of the needle (154) accommodates inside the safety device (102) and will not be exposed, preventing needle stick injuries.

Figure 9:
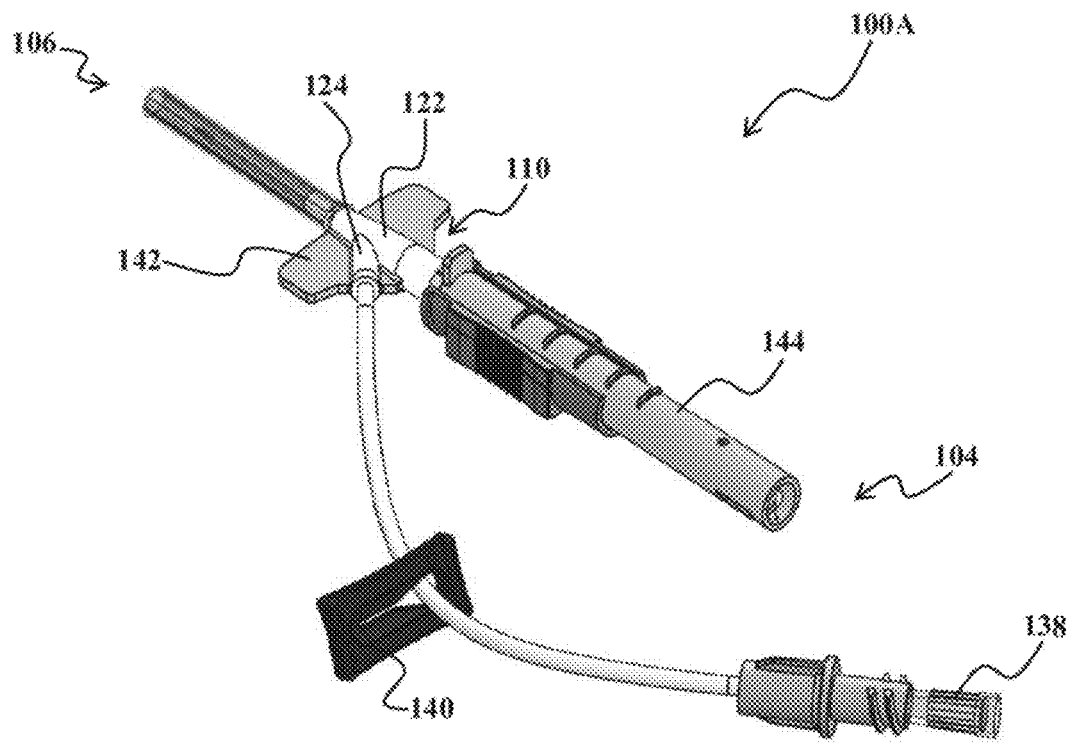
FIG. 9 shows a perspective view of a cannula having a safety device, according to a second exemplary embodiment of the present invention.
Figure 10:
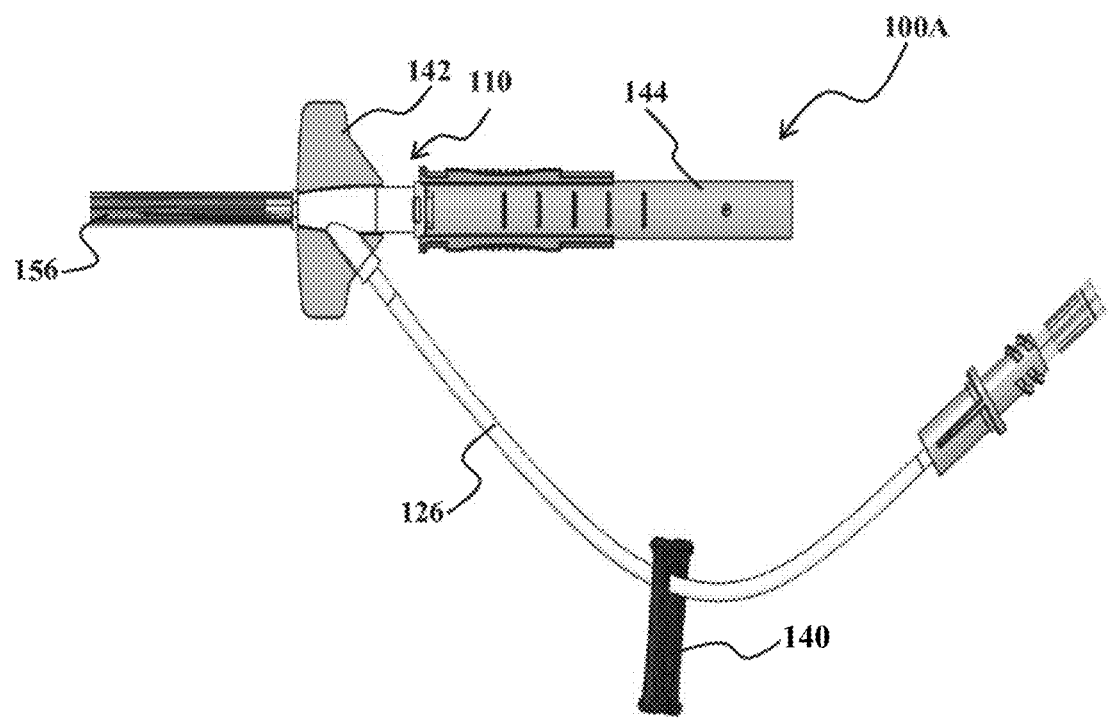
FIG. 10 shows a top view of the cannula shown in FIG. 9, where a needle is passed through a safety device for puncturing a vein.
Figure 11:
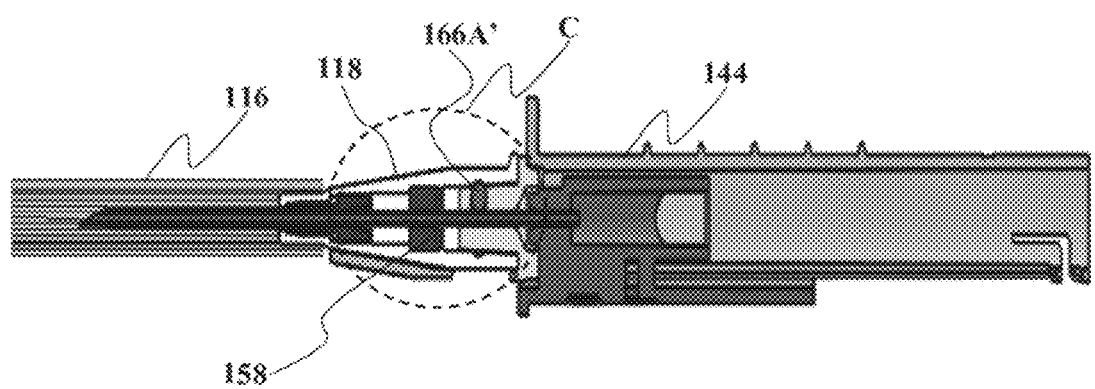
FIG. 11 shows a sectional view of the cannula shown in FIG. 9.

FIGS. 9 and 10 illustrate perspective and top views of a cannula (100A) having a safety device (102A), respectively, according to a second exemplary embodiment of the present invention. FIG. 11 shows a sectional view of the cannula (100A) shown in FIGS. 9 and 10, where a needle (154) is passed through a safety device (102A) for puncturing the vein.

Figure 12:
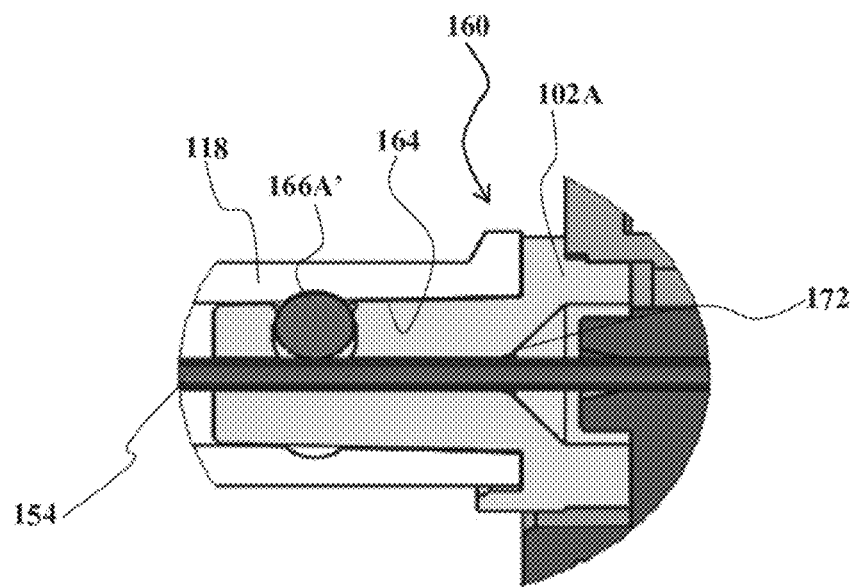
FIG. 12 shows a magnified view of portion "C" indicated in FIG. 11.

After passing through the safety device (102A) (shown in FIG. 12), the needle (154) passes through the rubber valve (158) disposed inside the body member (118), the catheter hub (110) and the catheter tube (116) for puncturing the vein. The safety device (102A) is fixedly connected to the distal end (160) of the elongated tubular member (144) and releasably connected to the body member (118) of the catheter assembly (108) at the end opposite to the distal end (160) (more clearly shown in FIG. 12). In FIGS. 11 and 12 it is illustrated that the needle (154) is passed through the safety device (102A) for puncturing the vein of the patient. FIG. 12 illustrates a magnified view of portion "C" indicated in FIG. 11. It is illustrated that the safety device (102A) is provided between the body member (118) of the catheter assembly (108) and the elongated tubular member (144). The cylindrical body portion (122) of the body member (118) includes the annular groove (162) at the inner surface (164) of the body member (118). The annular groove (162) in the body member (118) is adapted to engage with the locking element (166A') of the safety device (102A) when the needle (154) is passed through the safety device (102A). In the illustrated figure, the locking element (166A') is one solid spherical element (166A').

Figure 13:
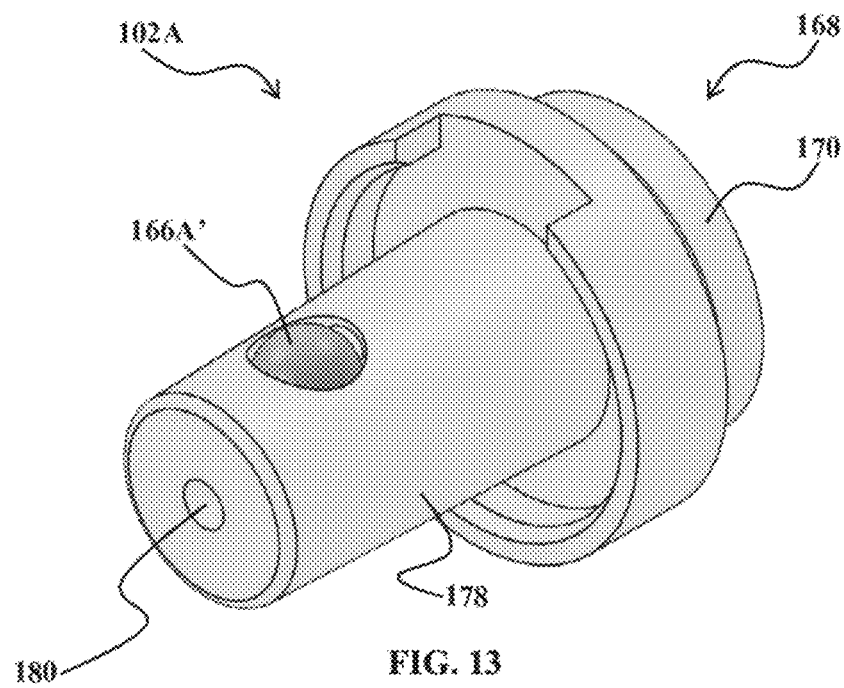
FIG. 13 shows a perspective view of the safety device shown in FIGS. 11-12, according to the second exemplary embodiment of the present invention.
Figure 14:
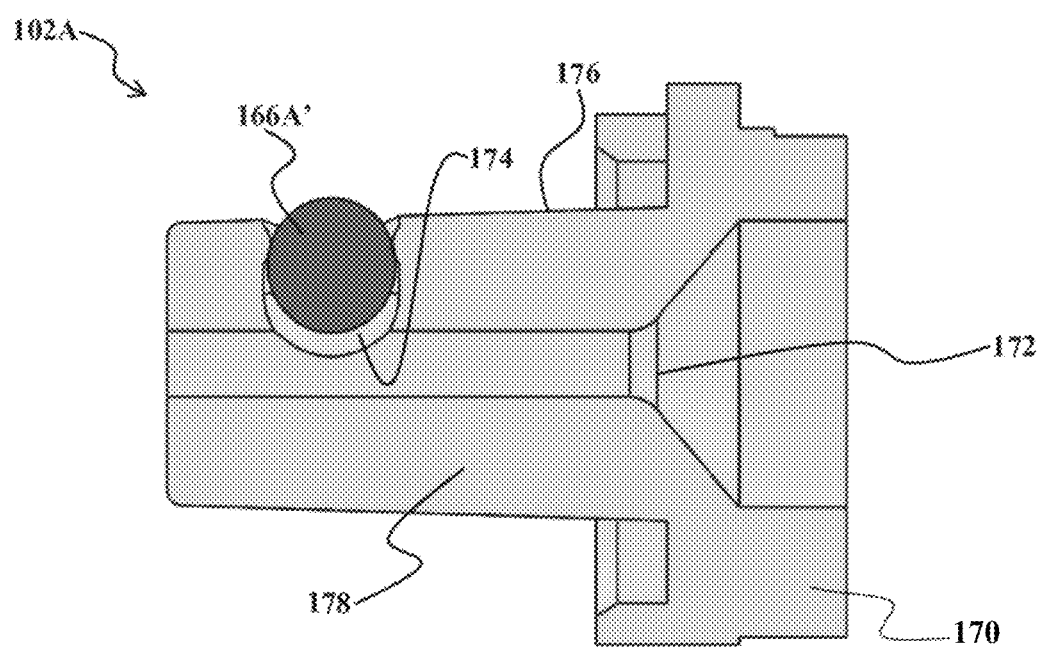
FIG. 14 shows a sectional view of the safety device shown in FIG. 13.

FIGS. 13 and 14 illustrate a perspective view and a sectional view of the safety device (102A), respectively, according to the second exemplary embodiment of the present invention. The safety device (102A) comprises the first end (168) having the circular base portion (170). The circular base portion (170) is fixedly connected with the distal end (160) of the elongated tubular member (144). In an exemplary embodiment, the circular base portion (170) of the safety device (102A) is press-fitted to the elongated tubular member (144) forming a unison between the safety device (102A) and the elongated tubular member (144). The circular base portion (170) is provided with the central hole (172) for passage of the needle (154). The safety device (102A) comprises one groove (174) on the outer surface (176) to accommodate the one locking element (166A'). In the illustrated embodiment, the safety device (102A) comprises the tubular portion (178) extending from the circular base portion (170) and includes the axial bore (180) forming the passage for the needle (154) from the central hole (172). The groove (174) is provided on the outer surface (176) of the tubular portion (178) and extends towards the axial bore (180) of the safety device (102A).

In the illustrated figures, the locking element (166A') is one solid spherical element (166A'). The solid spherical element may be in the form of a solid ball (166A') made of stainless steel material. It may be understood that the solid spherical element may be made of any other materials which are bio-compatible or non-reactive to the fluids passing through the cannula (100).

The groove (174) made on the outer surface (176) of the tubular portion (178) of the safety device (102A) has the same or substantially same or equal diameter as that of the diameter of the solid spherical element. This facilitates easy or smooth movement of the spherical ball outwardly when the needle (154) is passed through the axial bore (180) while puncturing the vein or withdrawn after puncturing the vein. In another exemplary embodiment, the diameter of the groove (174) may be less or more that the diameter of the solid spherical element. However, the diameters should be kept in such a manner that the movement of the spherical ball should not be hindered.

In the illustrated embodiments of FIGS. 13 and 14, the locking element or the solid ball (166A') of the safety device (102A) is adapted to engage with the annular groove (162) of the body member (118). This forms a locking engagement and a tight fit relationship between the elongated tubular member (144) and the catheter assembly (108) when the needle (154) is passed through the safety device (102A) for puncturing the vein of the patient.

Figure 15:
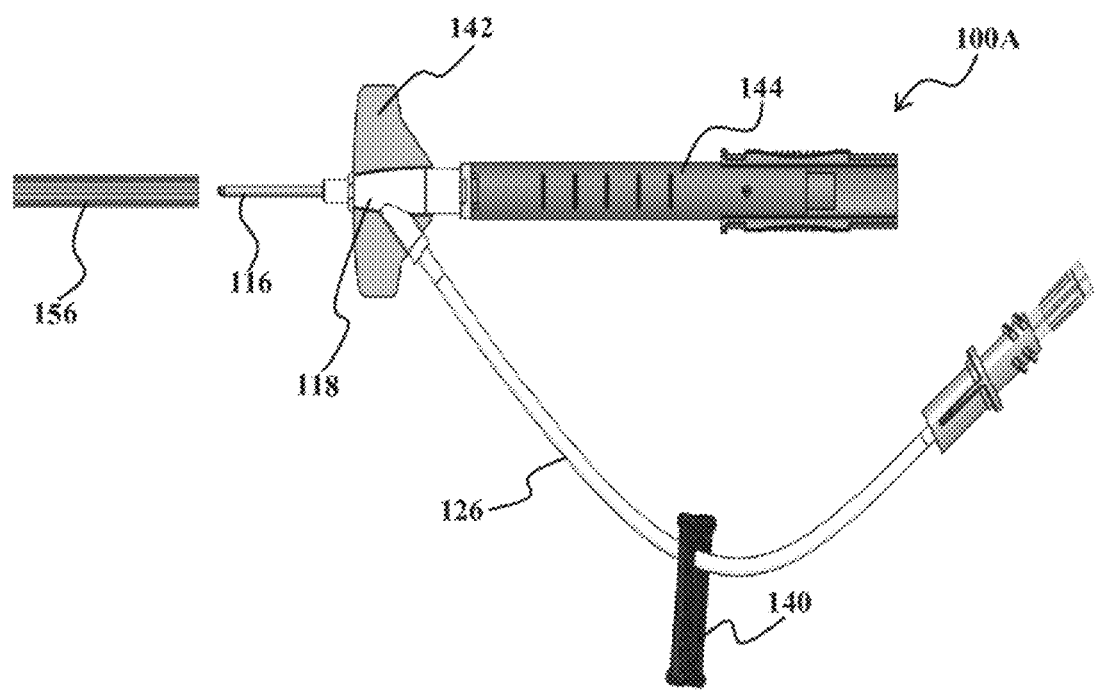
FIG. 15 shows a top view of the cannula shown in FIGS. 9 and 10, where a needle is withdrawn from the catheter assembly after puncturing the vein and a tip of the needle is arrested within the safety device.
Figure 16:
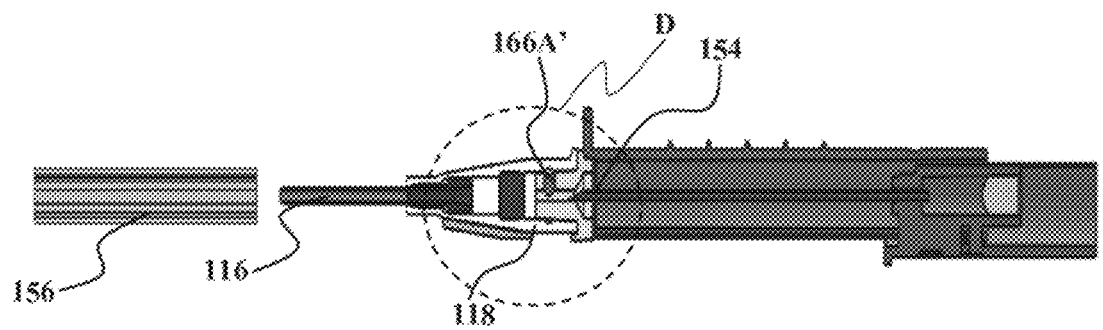
FIG. 16 shows a sectional view of the cannula, where a needle is withdrawn from the catheter assembly after puncturing the vein and a tip of the needle is arrested within the safety device.
Figure 17:
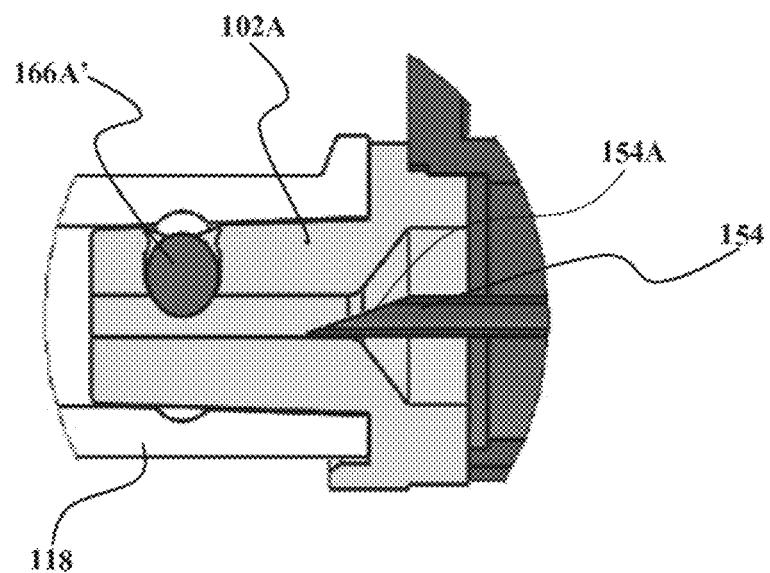
FIG. 17 shows a magnified view of portion "D" indicated in FIG. 16.

FIGS. 15 and 16 illustrate top and sectional views of the cannula (100A), respectively, shown in FIGS. 9-11, where the needle (154) is withdrawn from the catheter assembly (108) after puncturing the vein and the tip or bevel of the needle (154) is arrested within the safety device. FIG. 17 shows a magnified view of portion "D" indicated in FIG. 16, where the tip or bevel (154A) of the needle (154) is arrested or accommodated in the safety device (102A).

Figure 18:
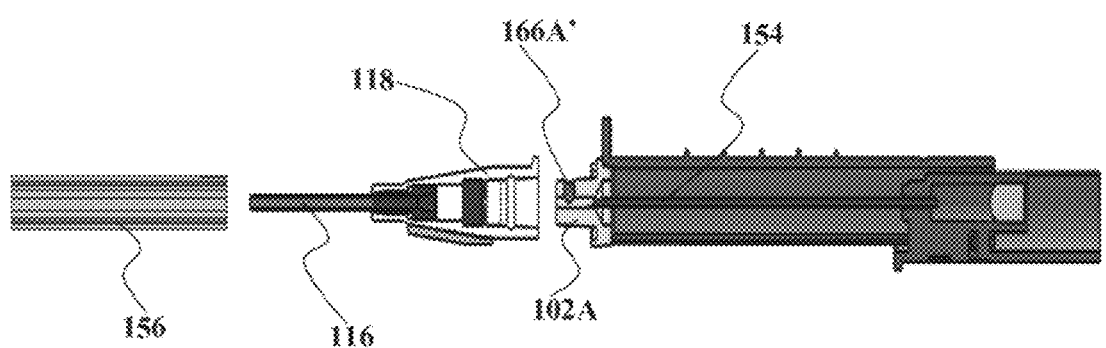
FIG. 18 shows a sectional view of the cannula, where the safety device is separated from a body member of the catheter assembly and the needle is arrested within the safety device.
Figure 19:
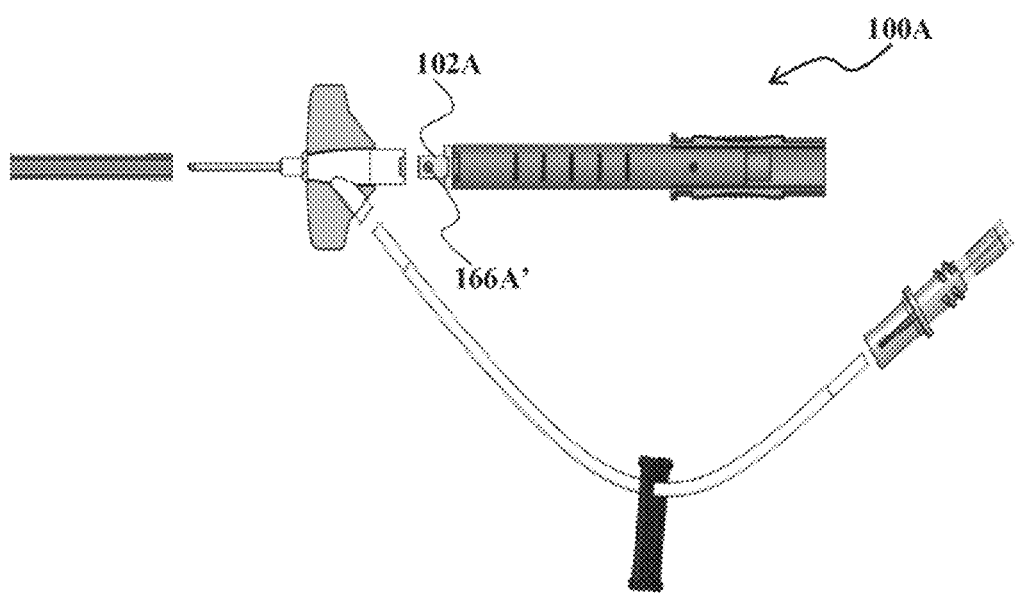
FIG. 19 shows a top view of the cannula shown in FIG. 18.

In the illustrated FIGS. 18 and 19, when the needle (154) is retracted from the catheter assembly (108) after puncturing the vein of the patient, the body member (118) which is in a tight fit relationship with the catheter assembly (108) is disengaged. The disengagement occurs because the locking element (solid ball) (166A') is disengaged or displaced from the annular groove (162), thereby disengaging the locking engagement between the elongated tubular member (144) and the catheter assembly (108), and separating the safety device from the body member of the catheter assembly. The separation of the safety device (102A) from the body member (118) of the catheter assembly (108) makes the needle (154) to be arrested within the safety device (102A). Thus, when the needle (154) is withdrawn after puncturing the vein, the needle tip or the bevel (154A) of the needle (154) accommodates inside the safety device (102A) and will not be exposed, preventing needle stick injuries.

Advantages

The disclosed safety device prevents the tip of the needle from coming in contact with the user after withdrawing the needle. The needle gets arrested within the safety device. That is to say, the safety device provides a safety mechanism such that the tip of the needle does not come in contact with the operator or the patient when the needle is withdraw after piercing the vein of the patient. Thus, serious injuries or infections that would have been caused by the needle are prevented.

The disclosed locking elements of solid spherical balls provides disengagement of the catheter assembly and the elongated tubular member, and the needle tip is accommodated or arrested inside the safety device attached to the elongated tubular member, preventing exposure of needle tip and needle stick injuries.

The disclosed locking elements of solid spherical balls of the safety device enable the easy removal of the needle by unlocking the locking engagement.

While aspects of the present invention have been particularly shown and described with reference to the embodiments above, it will be understood by those skilled in the art that various additional embodiments may be contemplated by modification of the disclosed device without departing from the scope of what is disclosed. Such embodiments should be understood to fall within the scope of the present invention as determined based upon claims and any equivalents thereof.

LIST OF REFERENCE NUMERALS AND REFERENCE SIGNS

100 Cannula
100A Cannula
102 Safety device
102A Safety device
104 First end of the cannula
106 Second end of the cannula
108 Catheter assembly
110 Catheter hub
112 Distal end of the catheter hub
114 Proximal end of a catheter tube
116 Catheter tube
118 Body member
120 Distal end of the body member
122 Cylindrical body portion
124 Tangential portion
126 Tube
128 One end of tube
130 Second end of tube
132 Flashback chamber
134 Female luer
136 Flow control hub
138 Filter
140 Slide clamp
142 Wing member
144 Elongated tubular member
146 Proximal end of the catheter assembly
148 Needle hub
150 Needle holder
152 Distal end of the needle holder
154 Needle
154A Tip or bevel of the needle
156 Needle protector
158 Rubber valve
160 Distal end of elongated tubular member
162 Annular groove in the body member
164 Inner surface of the body member
166 Locking elements
166A' Locking element
166A Solid balls
166A' Solid ball
168 First end of the safety device
170 Circular base portion
172 Central hole -continued 174 One or more grooves on the safety device
176 Outer surface of the safety device
178 Tubular portion of the safety device
180 Axial bore of the tubular portion of the safety device

The invention claimed is:

1. A safety intravenous cannula, comprising:
a catheter assembly comprising a catheter hub, the catheter hub having a distal end connected to a proximal end of a catheter tube, and a body member having a cylindrical portion along the catheter hub;
an elongated tubular member disposed at a proximal end of the catheter assembly;
a needle hub comprising a needle holder disposed inside the elongated tubular member, wherein a distal end of the needle holder is connected with a needle;
a safety device having a proximal portion fixedly connected to a distal end of the elongated tubular member and releasably connected to the body member of the catheter assembly,
wherein the body member is provided with an annular groove at an inner surface of the body member, and
wherein the safety device comprises one or more locking elements,
wherein the one or more locking elements of the safety device are adapted to engage with the annular groove of the body member, thereby forming a locking engagement and a tight fit relationship between the elongated tubular member and the catheter assembly when the needle is passed through the safety device for puncturing a vein of a patient, and
wherein when the needle is retracted from the catheter assembly after puncturing the vein of the patient, the body member which is in a tight fit relationship with the catheter assembly is disengaged by disengaging the one or more locking elements from the annular groove, thereby disengaging the locking engagement between the elongated tubular member and the catheter assembly, and separating the safety device from the body member of the catheter assembly, the needle being adapted to be arrested within the safety device.

2. The safety intravenous cannula of claim 1, wherein the safety device comprises a groove on an outer surface of the safety device to accommodate the one or more locking elements.

3. The safety intravenous cannula of claim 2, wherein the one or more locking elements are solid spherical elements made of a stainless steel material.

4. The safety intravenous cannula of claim 3, wherein the groove on the outer surface of the safety device has a diameter more than or equal to a diameter of the solid spherical elements.

5. The safety intravenous cannula of claim 3, wherein the solid spherical elements of the safety device are adapted to move outwardly to engage with the annular groove of the body member, thereby forming the locking engagement and the tight fit relationship between the elongated tubular member and the catheter assembly when the needle is passed through the safety device for puncturing the vein of the patient.

6. The safety intravenous cannula of claim 3, wherein when the needle is retracted from the catheter assembly after puncturing the vein of the patient, the body member which is in a tight fit relationship with the catheter assembly is disengaged by disengaging the solid spherical elements from the annular groove, thereby disengaging the locking engagement between the elongated tubular member and the catheter assembly, and separating the safety device from the body member of the catheter assembly, the needle being adapted to be arrested within the safety device.

7. The safety intravenous cannula of claim 1, wherein the proximal portion of the safety device has a circular base portion, the circular base portion fixedly connected with the distal end of the elongated tubular member and including a central hole.

8. The safety intravenous cannula of claim 7, wherein the safety device comprises a tubular portion extending from the circular base portion and including an axial bore forming a passage for the needle within the central hole.

9. The safety intravenous cannula of claim 8, wherein a groove provided on an outer surface of the tubular portion of the safety device extends towards the axial bore of the safety device.

\* \* \* \* \*